(12) United States Patent
Bumbalough et al.

(10) Patent No.: US 6,468,260 B1
(45) Date of Patent: Oct. 22, 2002

(54) SINGLE GEAR DRIVE BIDIRECTIONAL CONTROL HANDLE FOR STEERABLE CATHETER

(75) Inventors: Timothy Ray Bumbalough, Fullerton; Matthew F. Duncan, San Clemente; Bruce A. Christie, Upland, all of CA (US)

(73) Assignee: Biosense Webster, Inc., Diamond Bar, CA (US)

(*) Notice: Subject to any disclaimer, the term of this patent is extended or adjusted under 35 U.S.C. 154(b) by 0 days.

(21) Appl. No.: 09/546,310

(22) Filed: Apr. 10, 2000

Related U.S. Application Data
(60) Provisional application No. 60/133,709, filed on May 12, 1999, and provisional application No. 60/133,182, filed on May 7, 1999.

(51) Int. Cl.[7] .............................................. A61M 25/00
(52) U.S. Cl. ..................... 604/523; 604/528; 600/434
(58) Field of Search ........................... 604/95.04, 528, 604/523, 164.13; 600/434, 433

(56) References Cited

U.S. PATENT DOCUMENTS

| | | | |
|---|---|---|---|
| 4,203,430 A | 5/1980 | Takahashi | 128/4 |
| 4,207,873 A | 6/1980 | Kruy | 128/6 |
| 5,456,664 A | 10/1995 | Heinzelman et al. | 604/95 |
| 5,656,030 A | 8/1997 | Hunjan et al. | 604/95 |
| 6,171,277 B1 * | 1/2001 | Ponzi | 604/95.04 |

FOREIGN PATENT DOCUMENTS

| | | |
|---|---|---|
| EP | 0 928 601 A1 | 7/1999 |
| EP | 0 985 423 A2 | 3/2000 |

* cited by examiner

*Primary Examiner*—F. Daniel Lopez
*Assistant Examiner*—Dwayne White
(74) *Attorney, Agent, or Firm*—Christie, Parker & Hale, LLP

(57) ABSTRACT

A bi-directional steerable catheter comprising an elongated, tubular catheter body having at least one lumen, a tip section comprising flexible tubing having at least two lumens and fixedly attached to the distal end of the catheter body, and a control handle mounted to the proximal end of the catheter body. The control handle comprises a generally hollow handle housing, a generally tubular core extending longitudinally within the housing, and a generally circular spur gear rotatably mounted within the handle housing. First and second pistons are slidably mounted on the diametrically opposed sides of the spur gear and have puller wires attached to their distal ends. A longitudinally movable thumb control is fixedly attached to the first piston and accessible from outside the handle housing.

23 Claims, 11 Drawing Sheets

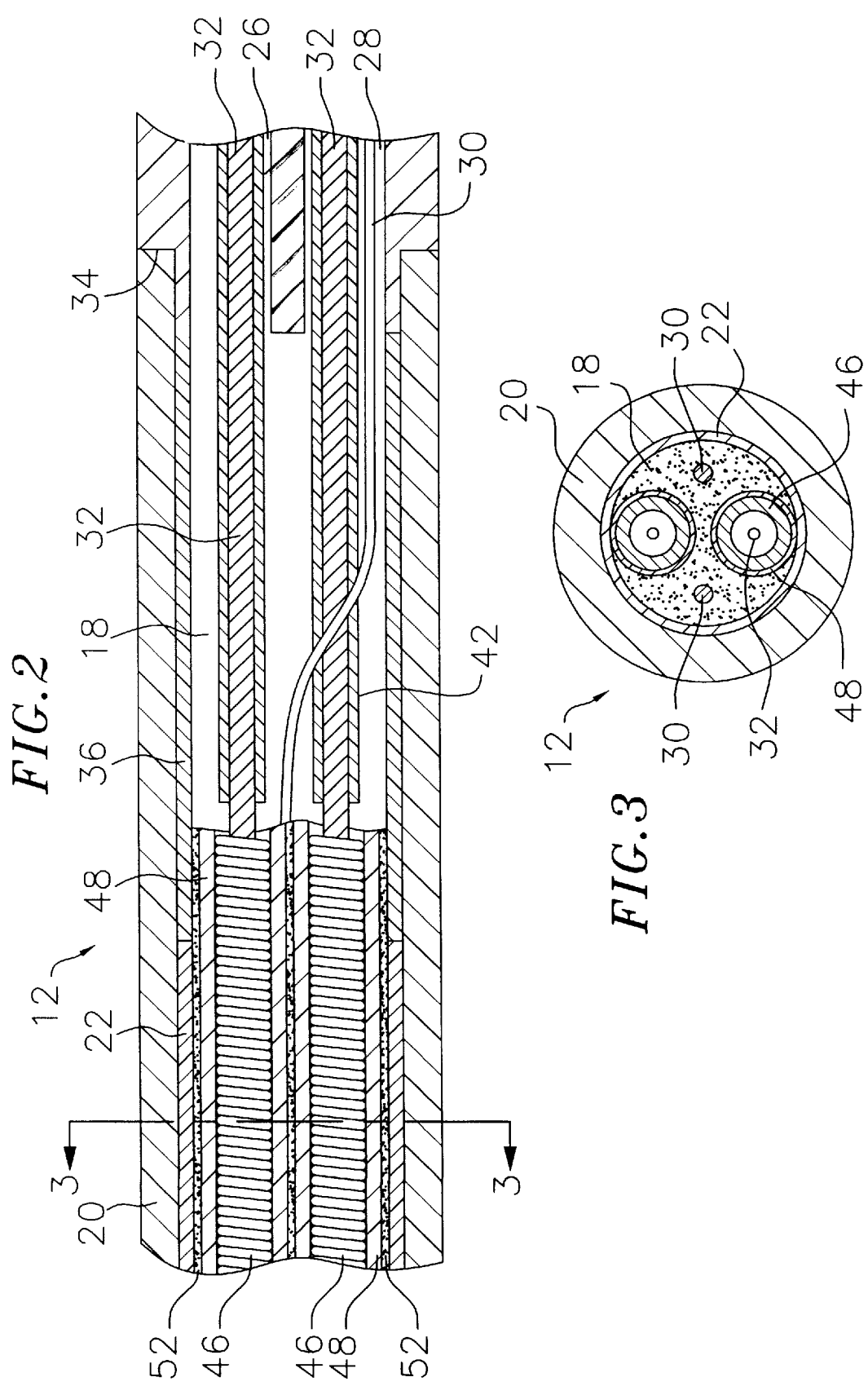

SINGLE GEAR DRIVE BIDIRECTIONAL CONTROL HANDLE FOR STEERABLE CATHETER

CROSS REFERENCE

This application claims priority to U.S. Provisional Patent Application Ser. No. 60/133,709, filed May 12, 1999, and U.S. Provisional Patent Application Ser. No. 60/133,182, filed May 7, 1999.

FIELD OF THE INVENTION

The present invention relates to an improved control handle for a bi-directional steerable catheter.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical-and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If a bidirectional catheter is desired, i.e., a catheter that can be deflected in more than one direction without rotating the catheter body, more than one puller wire becomes necessary. When two puller wires are used, however, it is undesirable for both wires to be moved simultaneously. The handle design disclosed in U.S. Pat. No. RE 34,502 is not suitable for a two puller wire system. Accordingly, a need exists for a control handle capable of independently moving each of two puller wires but preventing simultaneous movement of the puller wires.

SUMMARY OF THE INVENTION

The invention is directed to an improved bidirectional steerable catheter. In one embodiment, the catheter comprises an elongated, tubular catheter body having at least one lumen extending therethrough. A tip section comprising flexible tubing having at least two lumens extending therethrough is fixedly attached to the distal end of the catheter body.

A control handle is mounted to the proximal end of the catheter body. The control handle comprises a generally-hollow handle housing having inside and outside surfaces and a generally tubular core extending longitudinally within the housing. A generally-circular spur gear is rotatably mounted within the handle housing, the spur gear having teeth about its outer circumference. First and second pistons are slidably mounted on diametrically opposed sides of the spur gear and at least partially in surrounding relation to the tubular core within the handle housing. Each piston has an interior edge generally facing the interior edge of the other piston and comprises a series of teeth along its interior edge that engage the teeth of the spur gear so that proximal movement of one piston results in rotational movement of the spur gear and distal movement of the other piston. A longitudinally movable thumb control is fixedly attached to the first piston and accessible from outside the handle housing.

The catheter further comprises first and second puller wires having proximal and distal ends. Each puller wire extends from the control handle, through a lumen in the catheter body and into a lumen in the tip section. The distal end of each puller wire is fixedly attached to the tip section. The proximal end of the first puller wire is anchored to the first piston, and the proximal end of the second puller wire is anchored to the second piston.

Proximal movement of the thumb control relative to the handle housing results in proximal movement of the first piston and first puller wire relative to the handle housing and catheter body, which results in deflection of the tip section in the direction of the lumen into which the first puller wire extends. Distal movement of the thumb control relative to the handle housing results in distal movement of the first piston, causing proximal movement of the second piston and puller wire relative to the handle housing and catheter body, which results in deflection of the tip section in the direction of the lumen into which the second puller wire extends.

In another embodiment, the invention is directed to a catheter comprising a catheter body having a tubular wall, proximal and distal ends, and at least one lumen extending therethrough. A control handle is mounted to the proximal end of the catheter body. The control handle comprises a housing having proximal and distal ends and an interior core within the housing and attached to the catheter body. A fastener mechanically connects the handle housing to the core through an opening in the handle housing. The fastener comprises a body having a top side and a bottom side that fits within the opening in the handle housing and at least two flexible prongs extending from the underside of the body that mate with the core.

In another embodiment, the invention is directed to a catheter comprising a catheter body having a tubular wall, proximal and distal ends, and at least one lumen extending therethrough. A control handle is mounted to the proximal end of the catheter body. The control handle comprises a housing having proximal and distal ends, a tubular core within the housing and fixedly attached to the housing and catheter body, and a n interior member within the housing having proximal and distal ends and being longitudinally moveable relative to the housing and tubular core. A washer comprising a proximal ring and an outer wall extending distally therefrom is mounted about the tubular core. A flexible o-ring having inner and outer surfaces sits within the washer so that the outer surface of the o-ring is in contact with the outer wall of the washer and the inner surface of the o-ring is in contact with the core. A thumb control knob is threadably-engaged to the distal end of the interior member. When the thumb control knob is screwed onto the proximal piston, it compresses the o-ring into the washer, pressing the inner surface of the o-ring against the core so that the user can adjust the tension on the thumb control by screwing or unscrewing the thumb control.

DESCRIPTION OF THE DRAWINGS

These and other features of the advantages of the present invention will be better understood by reference to the following detailed description when considered in conjunction with the accompanying drawings wherein:

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3—3.

DETAILED DESCRIPTION

Figure 1:
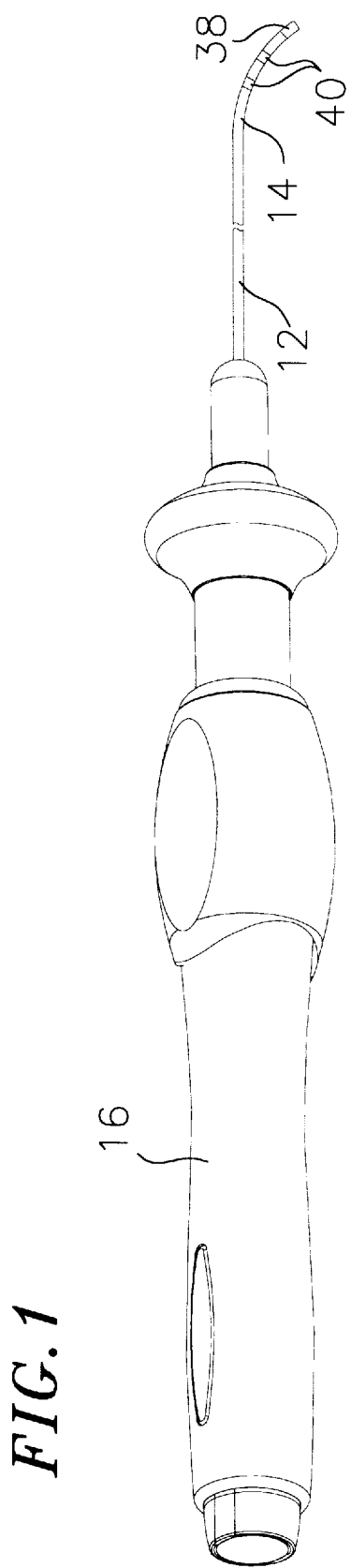
FIG. 1 is a side view of an embodiment of the catheter of the invention.

In a particularly preferred embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch. If desired, the stiffening tube can be omitted.

Figure 5:
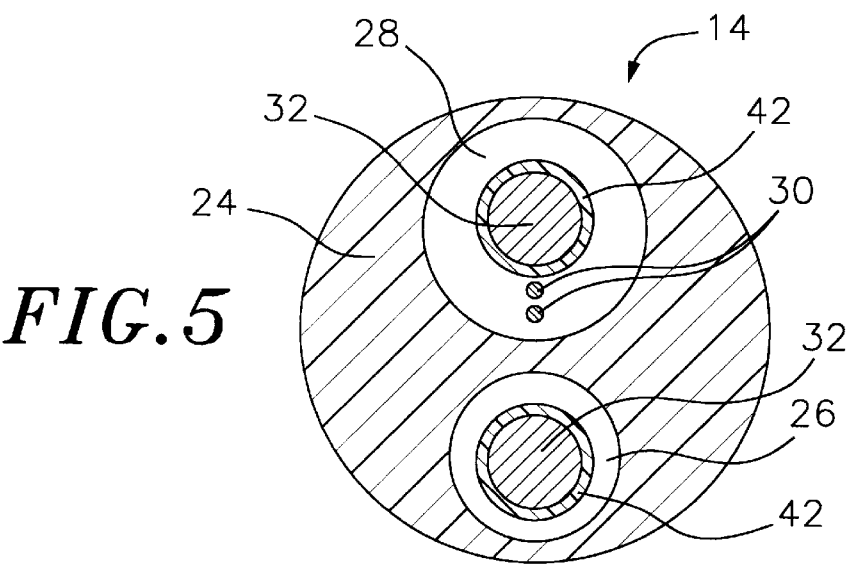
FIG. 5 is a transverse cross-sectional view of the tip section along line 5—5.
Figure 4:
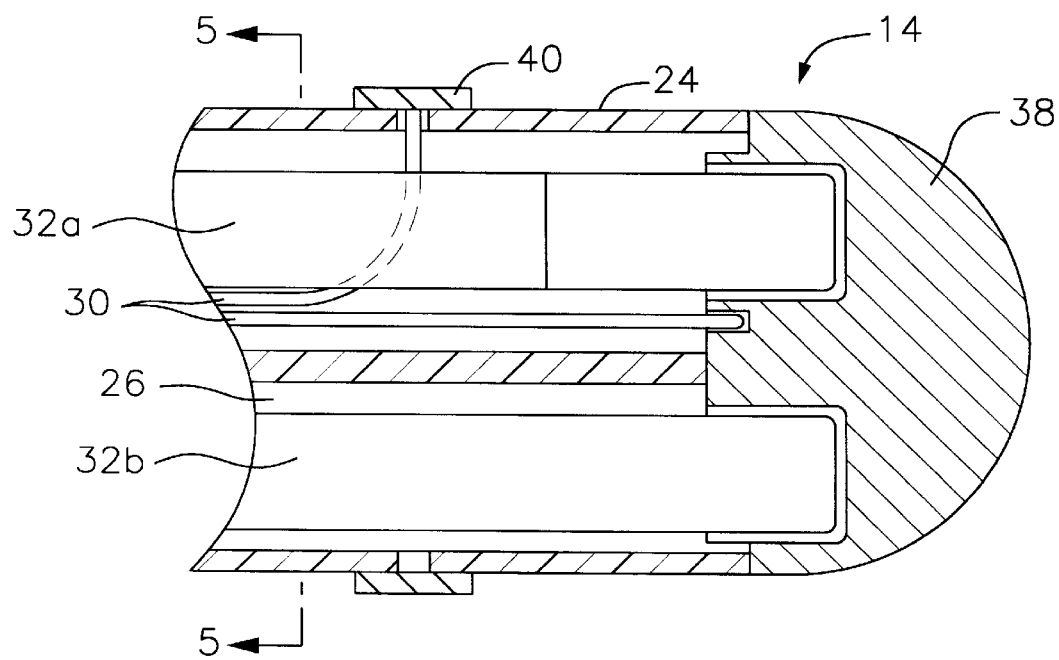
FIG. 4 is a side cross-sectional view of the distal end of the tip section shown in FIG. 2.

As shown in FIGS. 4 and 5, the tip section 14 comprises a short section of flexible tubing 24 having a first off-axis lumen 26 and a second off-axis lumen 28. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 8 french, more preferably about 6½ french or less.

The off-axis lumens 26, 28 extend through diametrically opposed halves of the tip section 14. In the depicted embodiment, the off-axis lumens 26, 28 are asymmetrical and therefore non-interchangeable. The first off-axis lumen 26 is smaller than the second off-axis lumen 28. In an 8 French or 7 French diameter catheter, where the tip section is 6½ French, it is preferred that the first off-axis lumen 26 has a diameter ranging from about 0.018 inch to about 0.025 inch, more preferably from about 0.018 inch to about 0.022 inch. Preferably, the second off-axis lumen 28 has a diameter ranging from about 0.022 inch to about 0.030 inch, more preferably from about 0.026 inch to about 0.028 inch. By using two rather than three lumens along a single diameter, the present design retains the simplified construction of the unidirectional deflectable steerable catheter described in U.S. Pat. No. Re 34,502, which is incorporated herein by reference. However, the number and size of the lumens in the tip section is not critical to the present invention and can vary as desired.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane.

A spacer 36 lies within the catheter body 12 between the distal end of the stiffening tube 22 and the proximal end of the tip section 14. The spacer 36 is preferably made of a material that is stiffer than the material of the tip section 14, e.g., polyurethane, but not as stiff as the material of the stiffening tube 22, e.g. polyimide. A spacer made of Teflon(& is presently preferred. A preferred spacer 36 has a length of from about 0.25 inch to about 0.75 inch, more preferably about 0.50 inch. Preferably the spacer 36 has an outer and inner diameter about the same as the outer and inner diameters of the stiffening tube 22. The spacer 36 provides a transition in flexibility at the junction of the catheter body 12 and the tip section 14 to bend smoothly without folding or kinking. If desired, the spacer 36 can be omitted.

As shown in FIG. 4, the distal end of the tip section 14 carries a tip electrode 38. Mounted along the length of the tip section 14 is a ring electrode 40. The length of the ring electrode 40 is not critical, but preferably ranges from about 1 mm to about 3 mm. Additional ring electrodes can be provided if desired. If multiple ring electrodes are used, they are spaced apart in any fashion as desired so long as their edges do not touch.

The tip electrode 38 and ring electrode 40 are each connected to a separate lead wire 30. Each lead wire 30 extends through the second off-axis lumen 28 in the tip section 14, through the central lumen 18 in the catheter body 12 and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to a ring electrode 40 is preferably accomplished by first making a small hole through the tubing 24. Such a hole can be created, for example, by inserting a needle through the tubing 24 and heating the needle sufficiently to form a permanent hole. A lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

Two puller wires 32 extend through the catheter 10. Each puller wire 32 extends from the control handle 16, through the central lumen 18 in the catheter body 12 and into one of the off-axis lumens 26 and 28 of the tip section 16. As described in more detail below, the proximal end of each puller wire 32 is anchored within the control handle 16 and the distal end of each puller wire 32 is anchored within the tip section 14.

Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 4, the puller wires 32 are both anchored in blind holes 37 in the tip electrode 38 by a welding or the like.

Figure 6:
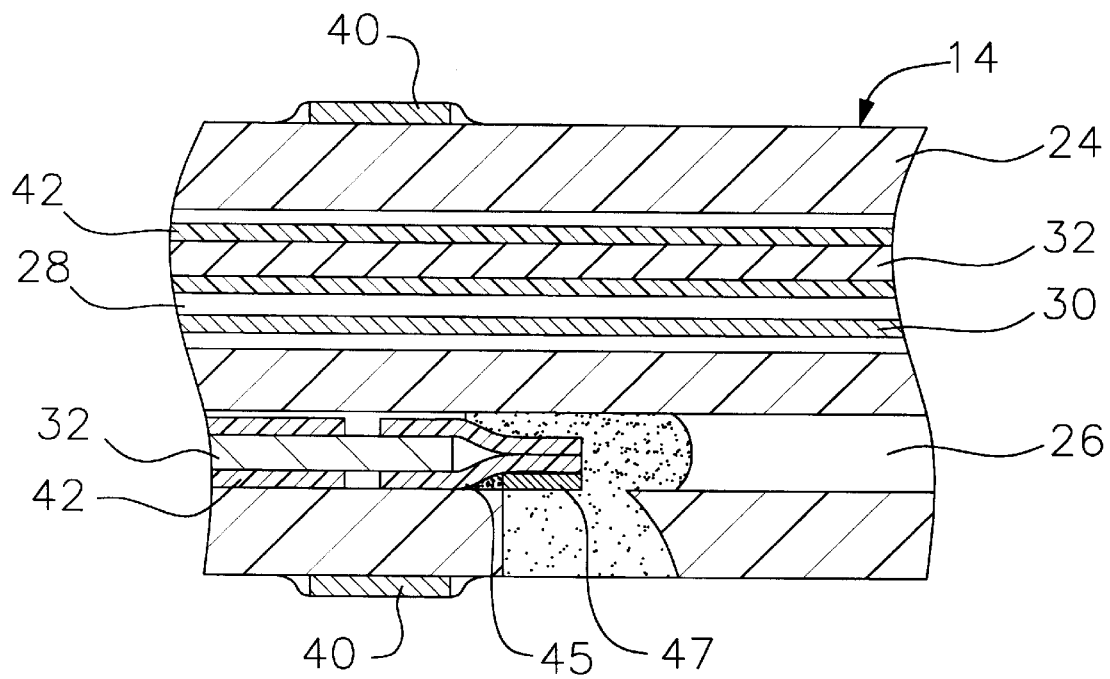
FIG. 6 is a transverse cross-sectional view of a catheter tip section according to the invention where the puller wires are anchored to the side walls of the tip section.
Figure 7:
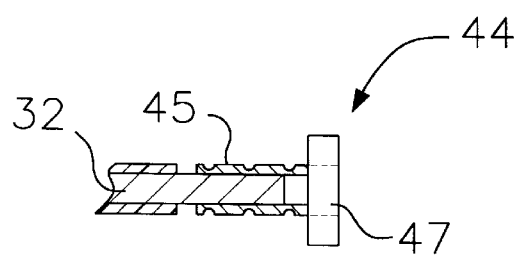
FIG. 7 is a longitudinal cross-sectional view of a preferred puller wire T-bar anchor.
Figure 8:
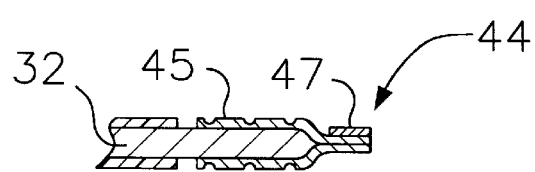
FIG. 8 is a longitudinal cross-sectional view of the puller wire T-bar anchor of FIG. 7 rotated 90° to show the cross-piece on end.

Alternatively, the puller wire 32 in the first off-axis lumen 26 can be anchored to the side wall of the tip section 14. As shown in FIGS. 6 to 8, the puller wire 32 is preferably attached by means of an anchor 44 fixedly attached to the distal end of the puller wire 32. The anchor 44 is formed by a metal tube 45, e.g., a short segment of hypodermic stock, that is fixedly attached, e.g. by crimping, to the distal end of the puller wire 32. The tube has a section that extends a short distance beyond the distal end of the puller wire 32. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14 resulting in an opening in the off-axis lumen 26 carrying the puller wire 32. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel (not shown), in the form of polyimide tubing or the like, can be provided to permit passage of the lead wire 30 through the glue so that this same puller wire anchor construction can be used in the second off-axis lumen 28. Other means for anchoring the puller wires 32 in the tip section 14 would be recognized by those skilled in the art and are included within the scope of the invention.

The catheter 10 further comprises two compression coils 46, each in surrounding relation to a corresponding puller wire 32. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. A non-conductive sheath 48 made of thin-walled polyimide tubing is presently preferred.

At the distal end of the catheter body, the two compression coils 46 are positioned in diametric opposition within the stiffening tube 22 and spacer 36 so that they can be aligned with the two off-axis lumens 26,28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

The distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26,28 of the tip section 14 and are anchored at their distal ends to the proximal end of the tip section 14 by a glue joint. In the depicted embodiment, where the compression coils 46 are each surrounded by a sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

Both glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

Within the off-axis lumens 26, 28, each puller wire 32 is surrounded by a plastic sheath 42, preferably made of Teflon®. The plastic sheathes 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Figure 9:
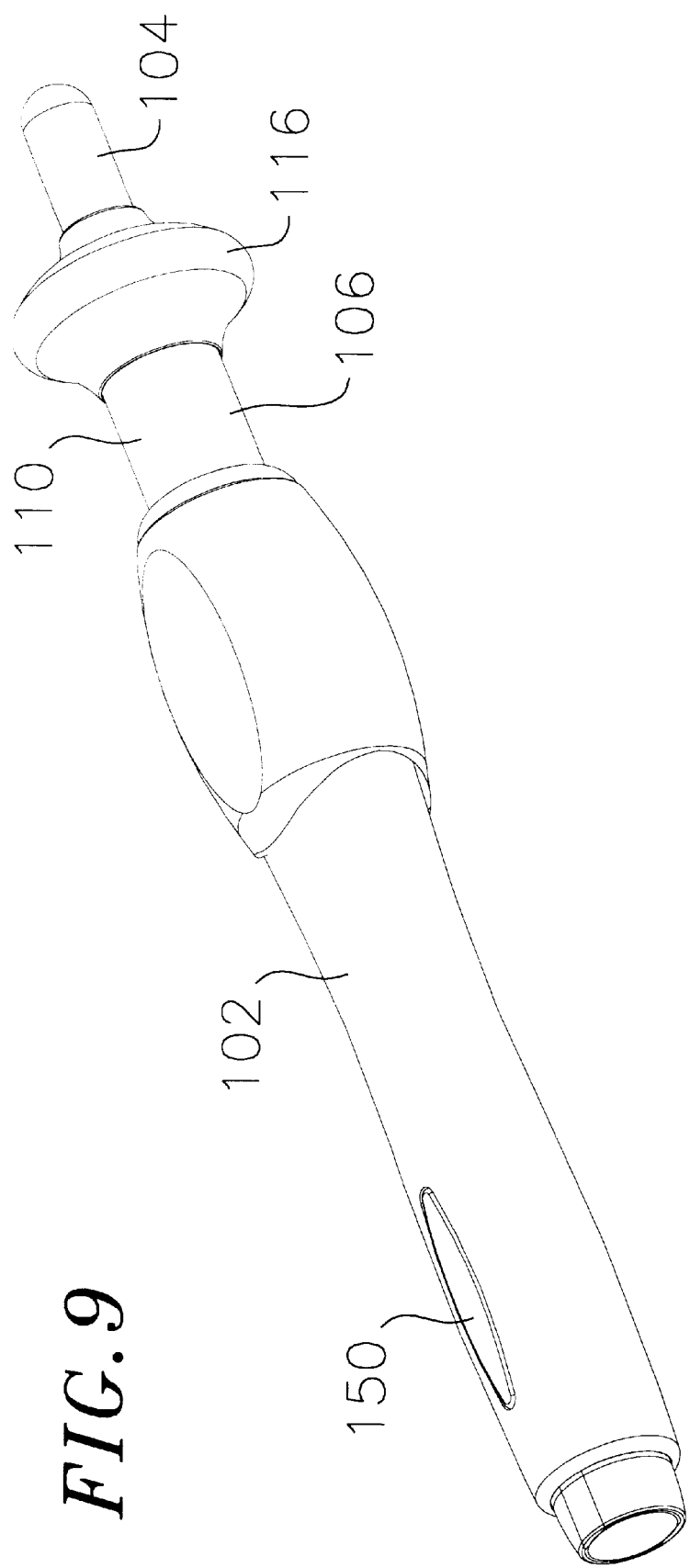
FIG. 9 is a perspective view of a handle in accordance with the invention.
Figure 10:
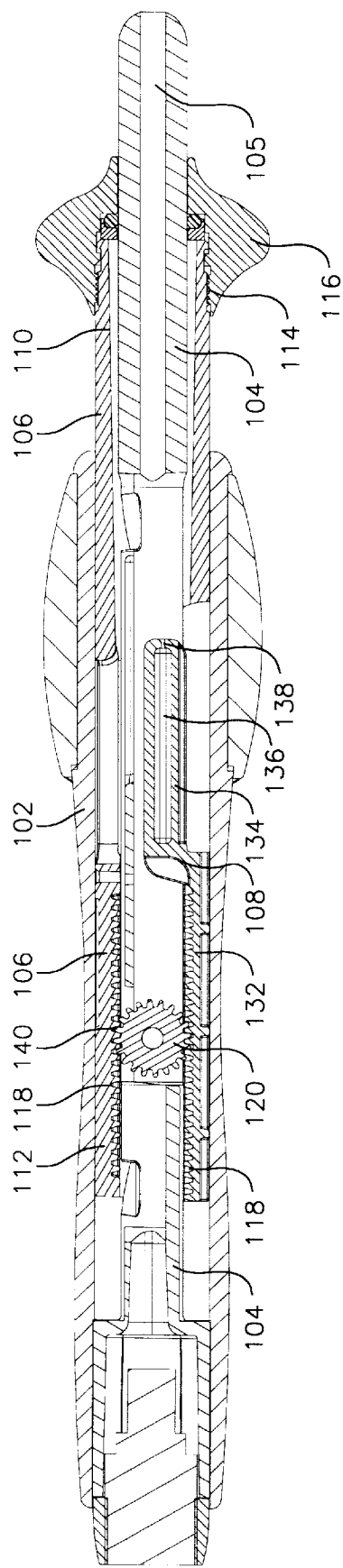
FIG. 10 is a side cross-sectional view of the handle of FIG. 9.
Figure 11:
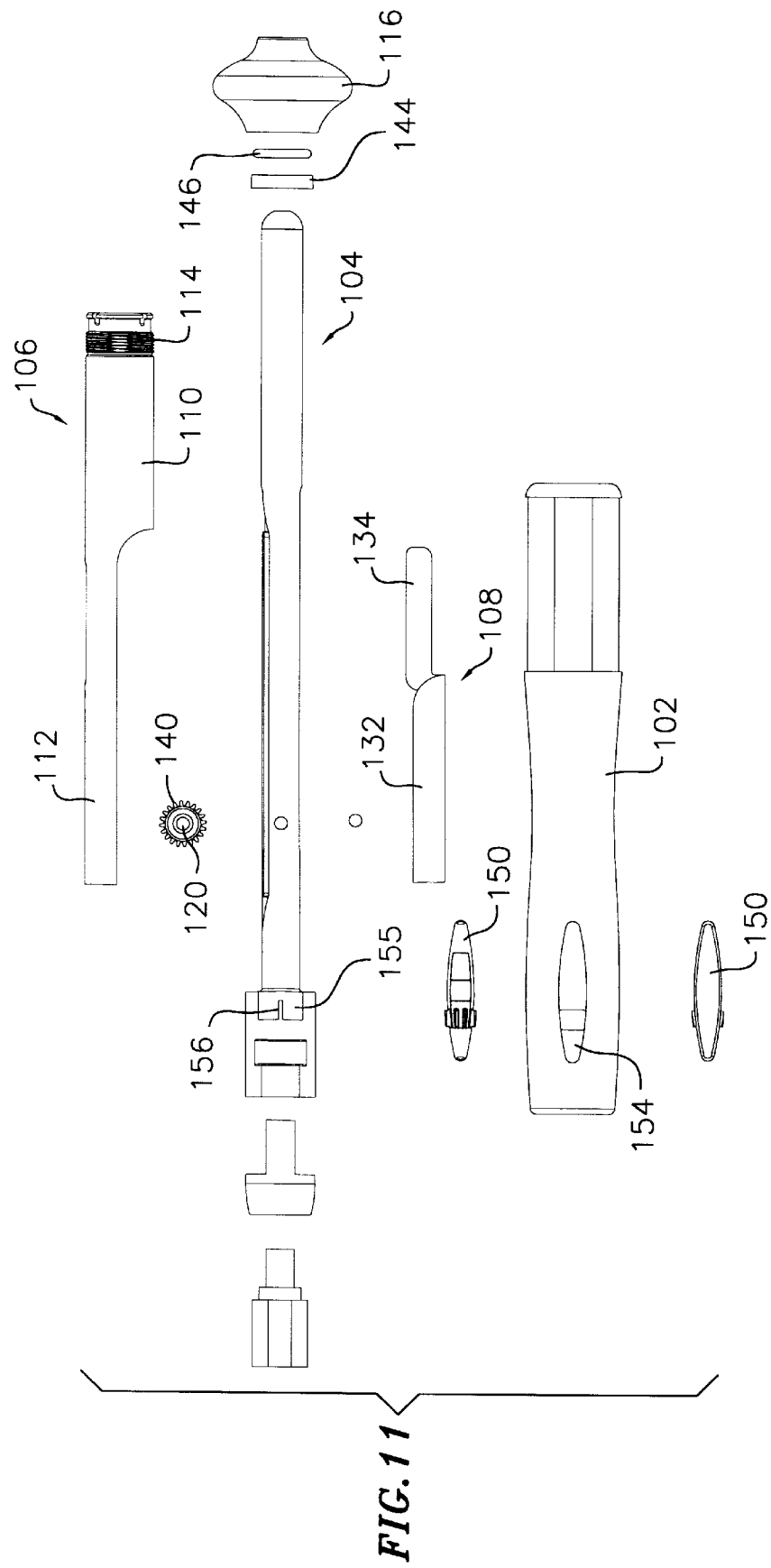
FIG. 11 is a side schematic view of the components of the handle of FIGS. 9 and 10 when the handle is not assemble.

Longitudinal movement of a puller wire 32 relative to the catheter body 12, which results in deflection of the tip section 14, is accomplished by suitable manipulation of the control handle 16. A suitable bidirectional control handle for use in the present invention is illustrated in FIGS. 9 to 11. The control handle 16 comprises a generally-hollow, preferably generally tubular, handle housing 102 having a longitudinal axis and proximal and distal ends and a generally tubular core 104 extending within the housing along its longitudinal axis. The core 104 is generally tubular along its length and has proximal and distal ends that extend beyond and outside the proximal and distal ends, respectively, of the housing 102. The catheter body 12 is fixedly attached in a passage 105 at the distal end of the core 104 by means of a glue joint and shrink sleeve, as is known to those skilled in the art. The puller wires 32, lead wires 30 and other cables, wires or tubes that extend through the catheter body extend through the passage 105 in the core 104.

Figure 13:
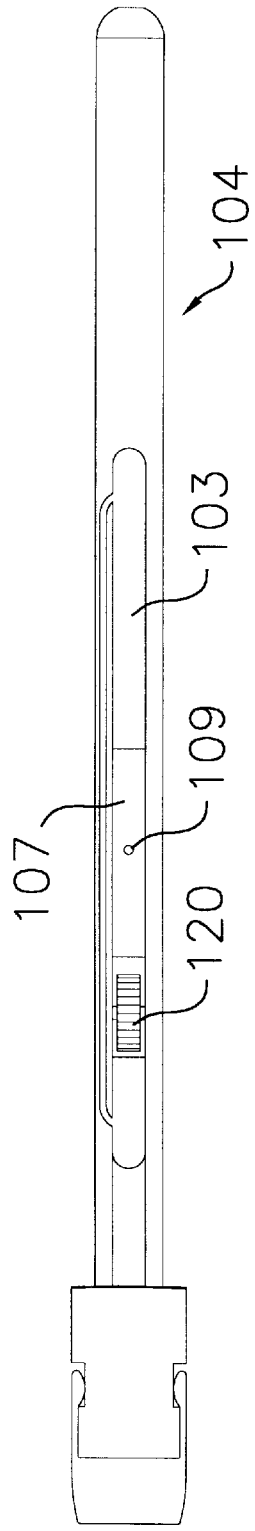
FIG. 13 is an alternative view of the core of the handle of FIGS. 9 to 11.

The core 104, as shown in more detail in FIG. 13, comprises two ovular slots 103 on opposite sides of the core that extend a portion of the length of the core, the functions of which are described in more detail below. A support member 107 is provided within the core 104 to add structural support to the core, and a small hole 109 is provided in the support member 107, the purpose of which is described below.

A primary piston 106 and a secondary piston 108 are mounted within the housing 102 generally in surrounding relation to the core 104, as described in more detail below. As shown best in FIG. 11, the primary piston 106 has a tubular distal region 110 and aproximal region 112 that has a generally semi-circular cross-section. As used herein, "generally semi-circular cross-section" refers to a generally-curved cross-section that may be greater or less than a semi-circle. The tubular distal region 110 is slidably mounted around the core 104 so that it completely surrounds the core. The proximal region 112 is shaped so that its inner surface fits generally against the tubular core, but only partially surrounds the core. When the handle 16 is assembled, a portion of distal region 110 extends outside the distal end of the housing 102. The distal region 110 of the primary piston 106 comprises threading 114 for mounting a thumb control 116 having corresponding internal threading (not shown) onto the primary piston. The inner surface of the proximal region 112 of the primary piston 106 comprises a series of teeth 118, which interact with a circular gear 120, described in more detail below.

Figure 12:
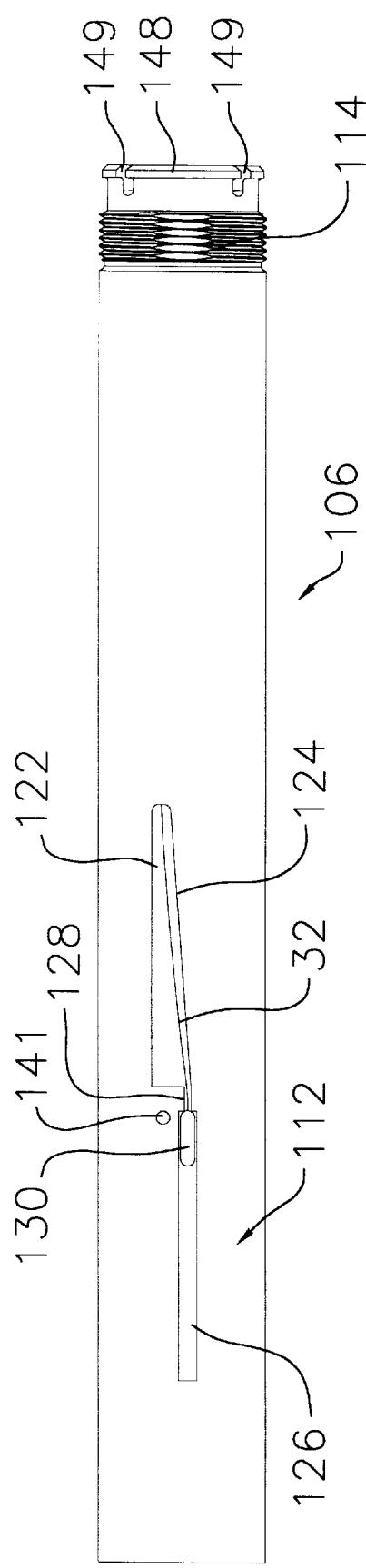
FIG. 12 is an alternative view of the primary piston of the handle of FIGS. 9 to 11.

FIG. 12 shows the primary piston 106 with the outer surface of the proximal region 112 turned toward the viewer. As shown best in FIG. 12, the proximal region 112 of the primary piston 106 is provided with a means for anchoring one puller wire 32 to the primary piston. The proximal region 112 of the primary piston 106 comprises a generally trapezoidal opening 122 having a long slanted edge 124. The opening 122 extends through the primary piston 106. A channel 126, which only extends a part of the way through the outer surface of the proximal piston, is provided proximal the opening 122. A small groove 128, having a width less than that of the channel 126, connects the channel to the opening 122. One puller wire 32 extends through the passage 105 in the core 104, out through one of the ovular slots 103 in the core, out through the opening 122 in the primary piston 106, through the small groove 128, and into the channel 126. The puller wire 32 is anchored in the channel 126 by means of a puller wire anchor 130, which preferably comprises a short piece of hypodermic stock that is fixedly attached, i.e., by crimping, to the proximal end of the puller wire 32 after it has passed through the small groove 128. The puller wire anchor 130 has a diameter greater than the width of the small groove 128 and thus prevents the proximal end of the puller wire 32 from being pulled through the small groove. The length of the opening 122 is limited such that, when the primary piston 106 is in its most distal position relative to the housing 102, the opening does not extend outside the housing. However, the opening 122 is preferably long enough so that the puller wire 32 extends through the opening at an angle rather than bending or kinking. The opening 122 can have any other size or shape as desired so long as it permits passage of the puller wire.

The secondary piston 108 has a proximal region 132 having a generally-semicircular cross-section with a generally rectangular stem 134 extending distally therefrom. The proximal region 132 of the secondary piston 108 is shaped so that its inner surface fits generally against the tubular core 104, in a manner similar to the proximal region 112 of the primary piston 106. In a particularly preferred embodiment, the proximal region 132 of the secondary piston 108 and the proximal region 112 of the primary piston 106 contact each other and together surround the core 104. The inner surface of the proximal region 132 of the secondary piston 108, like the primary piston 106, comprises a series of teeth 118, which interact with the circular gear 120, described further below.

The stem 134 of the secondary piston 108 is shaped to slidably fit within one of the slots 103 of the core 104. When the secondary piston 108 is moved distally, the stem 134 comes into contact with the distal end of the slot 103 in which it is mounted, controlling the extent of distal movement of the secondary piston. On one side, the stem 134 has a longitudinal channel 136 along its length, which terminates in a small longitudinal groove 138 having a width smaller than the width of the longitudinal channel. The second puller wire 32 extends through the passage 105 in the core 104, through the small longitudinal groove 138, and into the longitudinal channel 136. As with the primary piston, this puller wire 32 is anchored in the longitudinal channel 136 by means of a puller wire anchor 130 having a diameter greater than the width of the small longitudinal groove 138, thus preventing the proximal end of the puller wire 32 from being pulled through the small groove. Ideally, each puller wire 32 is anchored to a piston 106 or 108 in a position as close to the longitudinal axis of the core 104 as possible.

A circular gear 120 having teeth 140 about its circumference is mounted in the core 104, preferably by means of a dowel pin or the like. The teeth 140 of the circular gear 120 are aligned with the teeth 118 on the inner surfaces of the primary piston 106 and secondary piston 108. Accordingly, distal movement of the primary piston 106 results in proximal movement of the secondary piston 108, and proximal movement of the primary piston results in distal movement of the secondary piston. Thus, when the thumb control 116 is moved distally relative to the handle housing 102 and core 104, the primary piston 106 is also moved distally, and the secondary piston 108 is correspondingly moved proximally. The puller wire 32 attached to the secondary piston 108 also is pulled proximally, causing the tip section 14 to deflect in the direction of the side of the tip section to which that puller wire is anchored. The puller wire 32 attached to the primary piston 106, however, does not compress; instead the puller wire 32 and puller wire anchor 130 are provided free movement in the channel 126.

Conversely, when the thumb control 116 is moved proximally relative to the handle housing 102 and core 104, the primary piston 106 is also moved proximally and the secondary piston 108 is corresponding moved distally. The puller wire 32 attached to the primary piston 106 also is pulled proximally, causing the tip section 14 to deflect in the direction of the side of the tip section 14 to which that puller wire is anchored. The puller wire 32 and puller wire anchor 130 mounted in the secondary piston 108 are permitted free movement within channel 136, and thus the puller wire is not compressed.

In the depicted embodiment, when the catheter is in the neutral position, i.e., when the tip section 14 is not deflected, the primary piston 106 and secondary piston 108 are positioned so that the circular gear 120 is located at the midpoint of the teeth 18 on each piston. Accordingly, both pistons 106 and 108 can travel the same distance forward and backward. However, if desired, the pistons 106 and 108 can be positioned so that one of the pistons can travel a greater distance in a given direction than the other piston.

When assembling the catheter of the depicted embodiment, preferably the catheter body 12 and tip section 14 are assembled first. Next, the puller wires 32 are cut. In the depicted embodiment, when the primary piston 106 and secondary piston 108 are in the neutral position, the distal end 134 of the secondary piston is distal the proximal end 112 of the primary piston. Thus, the distal end of the puller wire 32 anchored to the primary piston 106 is proximal the distal end of the puller wire anchored to the secondary piston 108. Accordingly, the puller wires 32 are cut to be of different lengths, with the puller wire 32 anchored to the primary piston 106 being longer than the puller wire anchored to the secondary piston 32. When the tip section 14 is not deflected, both puller wires 32 should be close to being in tension.

To assemble the handle so that the puller wires are properly aligned, a hole 141 is provided in the primary piston 106, as shown in FIG. 12. An assembly pin (not shown) is placed through the hole 141 in the primary piston 106 and the hole 109 in the support member 107 of the core 104, described above. This position corresponds to the neutral position of the handle, i.e., where the tip section is not deflected. The puller wire anchor 130 is then positioned in the channel 126 of the primary piston 106. The catheter body 12 is pulled until there is just a small amount of tension on that puller wire, and then the catheter body is glued in place to the core 104. The assembly pin is then removed.

Figure 19:
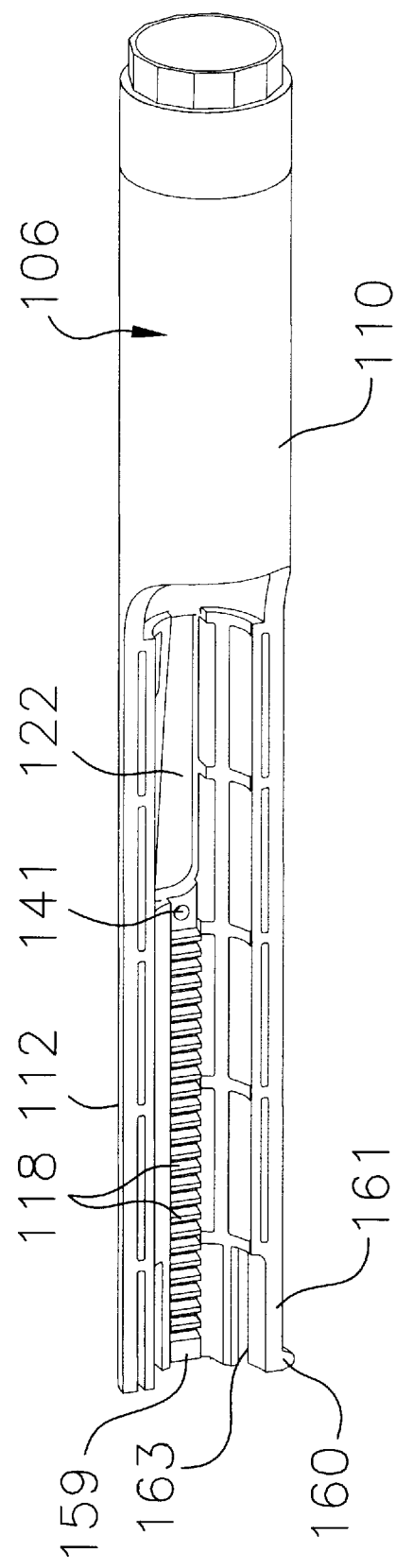
FIG. 19 is a side perspective view of an alternative embodiment of the primary piston.

In a particularly preferred embodiment, the two most proximal teeth 118 of the primary piston are replaced with a longer solid piece 159, as shown in FIG. 19. When the primary piston is moved distally, the teeth of the circular gear come into contact with the longer solid piece 159, preventing further distal movement of the primary piston.

When a physician is performing a procedure using the above-described catheter, it is desirable for the physician to be able to determine when the catheter is in the neutral position, i.e., when the tip section is not deflected. Accordingly, in a preferred embodiment, the center teeth of the primary piston are angled or skewed. The user can hear and feel when the teeth of the circular gear come into contact with the angled center teeth, notifying the user that the catheter is in the neutral position.

Figure 18:
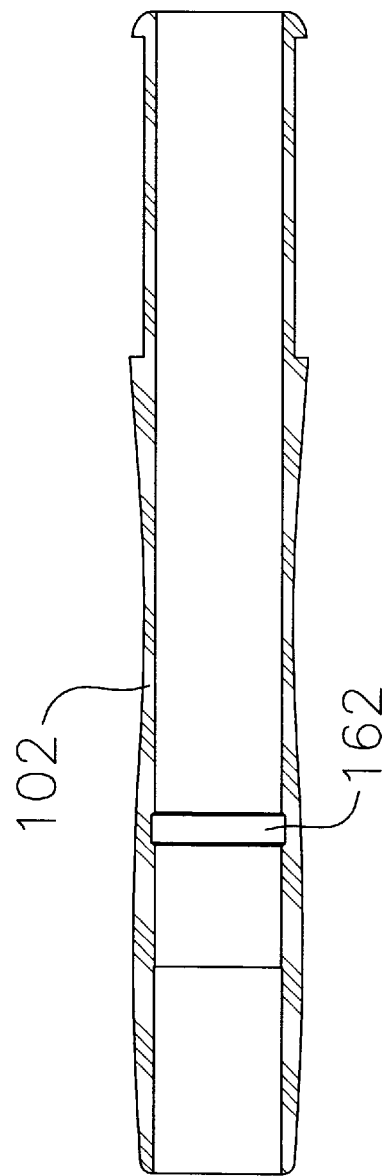
FIG. 18 is a side cross-sectional view of the inside of the handle housing.

In an alternate design, as shown in FIGS. 18 and 19, the primary piston 106 comprises a tab 160 at its proximal end that extends radially outwardly. The tab 160 is formed on a finger 161 that is separated from the proximal end of the primary piston by a slot 163 to provide the finger 161 some flexibility. The housing 102 has a groove 162 on its inside surface. The groove 162 is positioned so that the tab 160 is aligned with the groove when the catheter is in the neutral position. As the primary piston 106 is slid longitudinally relative to the housing 102, the tab 160 interacts with the groove 162, which can be heard and felt by the user, indicating to the user that the catheter is in the neutral position. The flexibility of the finger 161 permits the tab 160 to fit within the housing 102 when it is not aligned with the groove 162 and to more easily slide in and out of the groove.

Figure 20:
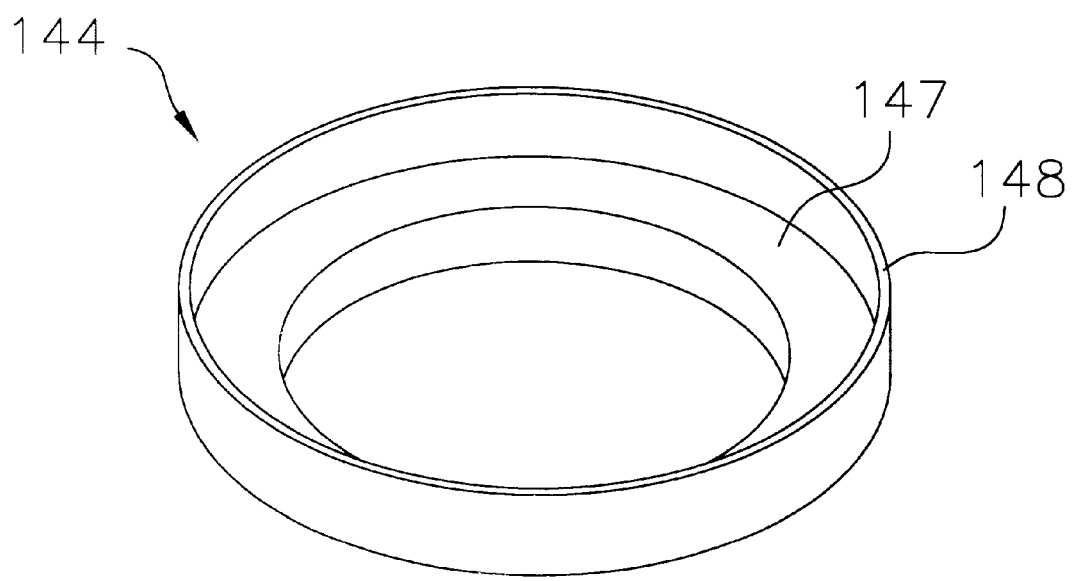
FIG. 20 is a perspective view of a washer according to the invention.
Figure 21:
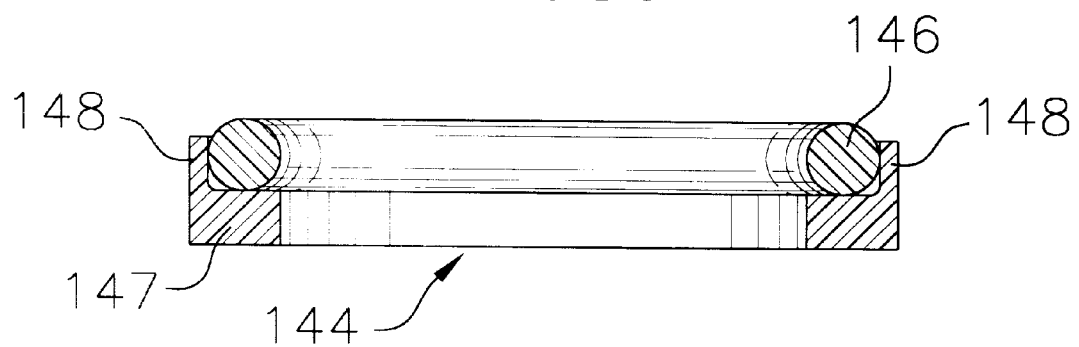
FIG. 21 is a cross-sectional view of an o-ring mounted in a washer according to the invention.

In a preferred embodiment, a washer 144 is mounted about the core 104 at the distal end of the primary piston 106. As shown in FIGS. 20 and 21, the washer 144 comprises a flat, O-shaped proximal ring 147 with an outer edge and an inner edge. An outer wall 148 extends distally from the outer edge of the proximal ring. By this design, the proximal end of the washer 144 is closed, but the distal end is open. The washer is preferably made out of the same material as the handle housing.

A flexible o-ring 146, made of plastic, rubber or the like, is provided having an outer surface, an inner surface, a proximal surface and a distal surface. The o-ring 146 sits in the open distal end of the washer 144 so that its proximal surface is in contact with the distal surface of the proximal ring of the washer, its outer surface is in contact with the outer wall 148, and its inner surface is in contact with the core 104.

With this design, when the thumb control 116 is screwed onto the proximal piston 106, it compresses the o-ring 146 into the washer 144, forcing the inner surface of the o-ring against the core 104. The user can adjust the tension on the thumb control 116 by screwing or unscrewing the thumb control, thus adjusting the pressure of the thumb control on the o-ring. Alternatively, the washer can be integral with the distal end of the primary piston. In other words, the distal end of the primary piston can be designed to incorporate a region into which the o-ring can fit to perform the same function, e.g., having a proximal ring and an outer wall extending distally from the proximal ring.

In a particularly preferred embodiment, an additional mechanism is provided to prevent the user from completely unscrewing the thumb control 116 when adjusting the tension. As shown in FIG. 12, the distal end of the primary piston 106 comprises a circumferential lip 148. A corresponding circumferential groove (not shown) is provided inside the thumb control 116. The outer diameter of the lip 148 is greater than the inner diameter of the thumb control 116, but less than the inner diameter of the circumferential groove of the thumb control. Cuts 149 are provided about the circumference of the lip 148 to provide flexibility to the lip so that the lip can be assembled into the circumferential groove. The length of the circumferential groove is greater than the length of the lip. Thus, the user can make adjustments to the tension of the thumb control, while maintaining the lip within the circumferential groove. However, the interaction between the lip and circumferential groove maintains the thumb control in place over the primary piston.

Figure 17:
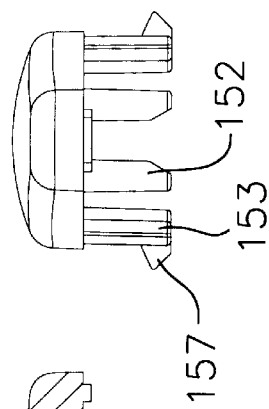
FIG. 17 is an end view of a fastener for use with the inventive handle.
Figure 14:
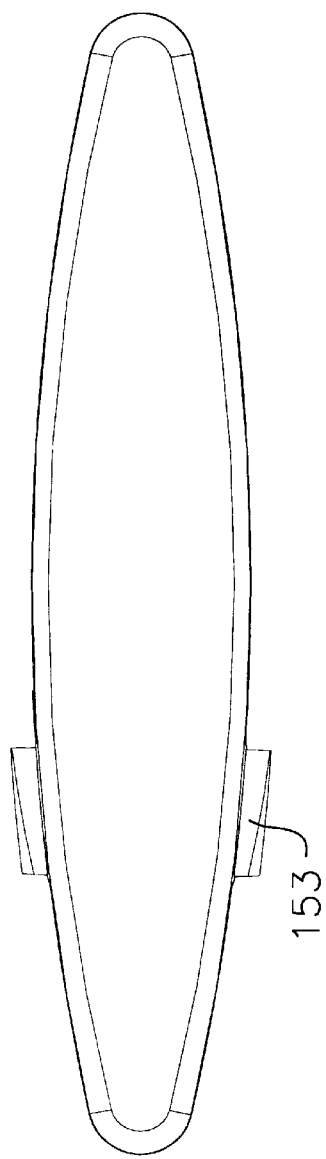
FIG. 14 is a top view of a fastener for use with the inventive handle.
Figure 15:
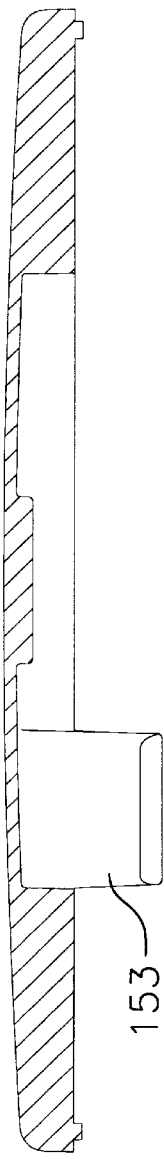
FIG. 15 is a side view of a fastener for use with the inventive handle.
Figure 16:
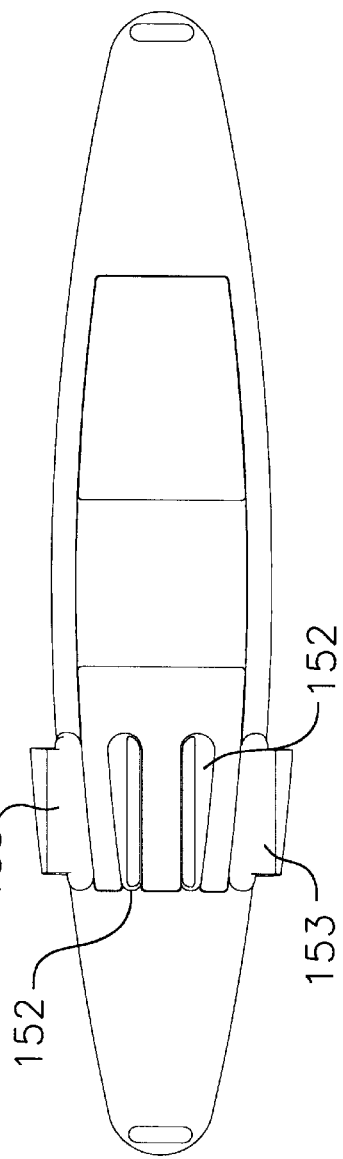
FIG. 16 is a bottom view of a fastener for use with the inventive handle.

In another preferred embodiment, a fastener 150 is provided to maintain the handle housing 102 in place over the core 104. FIGS. 14 to 17 show a preferred fastener 150 in accordance with the invention. The fastener 150 has a generally ovular (or jewel) shape. The top side, as shown in FIG. 14, is generally flat, but may be slightly curved to match the curved contour of the handle housing 102. The bottom side, as shown in FIGS. 15 to 17, comprises two inner prongs 152 and two outer prongs 153. The prongs 152 and 153 are received by the proximal end of the core 104, shown best in FIG. 11. Specifically, the proximal end of the core 104 comprises a recess 155 separated by tab 156. The prongs 152 and 153 extend into the recess 155, and the inner prongs 152 fit tightly around the tab 156 to maintain the fastener 150 in place. The handle housing 102 comprises an opening 154 corresponding in size and shape to the fastener 150. When the handle is assembled, the fastener 150 is snapped into place in the handle housing, with the prongs 152 and 153 being received by the distal end of the core 104, keeping the handle housing in place over the core. The outer prongs 153 comprise outwardly extending ears 157. When the fastener is snapped into the opening 154 of the housing 102, the ears 157 extend under the opening to keep the fastener in place in the handle housing. The fastener also provides a means for engraving or labeling the handle. The fastener can be provided with a design, trademark, or other insignia relevant to the catheter, thus making it unnecessary to manufacture the handle housing with the insignia directly thereon. The inventive fastener can be used with any catheter handle design having a hollow housing and a core member of some sort in the housing to which the housing is to be fixedly attached.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bidirectional steerable catheter comprising:
   an elongated, tubular catheter body having proximal and distal ends and at least one lumen extending therethrough;
   a tip section comprising flexible tubing having proximal and distal ends and at least two lumens extending therethrough, the proximal end of the tip section being fixedly attached to the distal end of the catheter body;
   a control handle mounted to the proximal end of the catheter body, the control handle comprising:
      a generally-hollow handle housing having proximal and distal ends and inside and outside surfaces,
      a generally tubular core extending longitudinally within the housing,
      a generally-circular spur gear rotatably mounted within the handle housing, the spur gear having teeth about its outer circumference, and
      first and second pistons slidably mounted on diametrically opposed sides of the spur gear and at least partially in surrounding relation to the tubular core within the handle housing, each having an interior edge generally facing the interior edge of the other piston and comprising a series of teeth along its interior edge that engage the teeth of the spur gear, whereby proximal movement of one piston results in rotational movement of the spur gear and distal movement of the other piston;
   a longitudinally movable thumb control fixedly attached to the first piston and accessible from outside the handle housing; and
   first and second puller wires having proximal and distal ends, each puller wire extending from the control handle, through a lumen in the catheter body and into a lumen in the tip section, the distal end of each puller wire being fixedly attached to the tip section, the proximal end of the first puller wire being anchored to the first piston and the proximal end of the second puller wire being anchored to the second piston;
   whereby proximal movement of the thumb control relative to the handle housing results in proximal movement of the first piston and first puller wire relative to the handle housing and catheter body, which results in deflection of the tip section in the direction of the lumen into which the first puller wire extends; and further whereby distal movement of the thumb control relative to the handle housing results in distal movement of the first piston, causing proximal movement of the second piston and puller wire relative to the handle housing and catheter body, which results in deflection of the tip section in the direction of the lumen into which the second puller wire extends.

2. A bidirectional steerable catheter according to claim 1, wherein the spur gear is mounted in the core.

3. A bidirectional steerable catheter according to claim 1, wherein the thumb control is mounted on the distal end of the first piston.

4. A bidirectional steerable catheter according to claim 1, wherein the first piston has at least one opening therethrough for passage of a puller wire.

5. A bidirectional steerable catheter according to claim 1, wherein:

the first piston has a tubular distal region that completely surrounds the core and a proximal region having a generally-semicircular cross-section that partially surrounds the core; and the second piston comprises a proximal region having a generally-semicircular cross-section that partially surrounds the core;

whereby the proximal region of the secondary piston and the proximal region of the primary piston contact each other and together completely surround the core.

6. A bidirectional steerable catheter according to claim 1, wherein the gear teeth on the first piston are skewed in the area in contact with the spur gear when the tip section is not deflected, the interaction between the angled gear teeth and the spur gear providing audible and tactile responses to enable the user to sense when the tip section is not deflected.

7. A bidirectional steerable catheter according to claim 1, wherein the distal end of the first piston comprises an exterior circumferential lip, and wherein the thumb control comprises a corresponding interior circumferential groove, the exterior lip having an outer diameter larger than the inner diameter of the thumb control but smaller than the inner diameter of the interior circumferential groove, and the interior groove having a length greater than the length thickness of the exterior lip.

8. A catheter according to claim 1, wherein the washer is integral with the distal end of the interior member.

9. A catheter according to claim 1, wherein the washer is mounted distal to the interior member.

10. A bidirectional steerable catheter according to claim 1, wherein the first piston has a tubular distal region that complete surrounds the core and a proximal region that partially surrounds the core.

11. A bidirectional steerable catheter according to claim 10, wherein the proximal region has a generally-semicircular cross-section.

12. A bidirectional steerable catheter according to claim 1, wherein the second piston comprises a proximal region having a generally-semicircular cross-section that partially surrounds the core.

13. A bidirectional steerable catheter according to claim 12, wherein the second piston further comprises a generally rectangular stem extending distally from the proximal region.

14. A bidirectional steerable catheter according to claim 13, wherein the generally rectangular stem is slidably mounted within a longitudinal slot within the core.

15. A bidirectional steerable catheter according to claim 1, wherein the first piston comprises a tab extending radially outward, and wherein the control handle housing comprises a groove on its inside surface that is capable of accommodating the tab and positioned so that the tab is seated in the groove when the tip section is not deflected.

16. A bidirectional steerable catheter according to claim 15, wherein the tab is positioned at the end of a flexible finger extending longitudinally from the proximal end of the first piston.

17. A catheter comprising:

a catheter body having a tubular wall, proximal and distal ends, and at least one lumen extending therethrough;

a control handle mounted to the proximal end of the catheter body, the control handle comprising:

a housing having proximal and distal ends, an interior core within the housing and attached to the catheter body, and a fastener mechanically connecting the handle housing to the core through an opening in the handle housing, the fastener comprising a body having a top side and a bottom side that fits within the opening in the handle housing and at least two flexible prongs extending from the underside of the body that mate with the core.

18. A bidirectional steerable catheter according to claim 17, wherein the fastener body has a generally ovular shape.

19. A bidirectional steerable catheter according to claim 17, wherein the fastener body is generally flat.

20. A bidirectional steerable catheter according to claim 17, wherein the fastener is provided with a design or other insignia relevant to the catheter.

21. A bidirectional steerable catheter according to claim 17, wherein the fastener comprises two pairs of flexible prongs, each pair comprising an outer prong and an inner prong, wherein each pair of prongs is received by a recess in the core.

22. A bidirectional steerable catheter according to claim 21, wherein the outer prongs comprise outwardly extending ears, so that, when the fastener is snapped into the opening of the handle housing, the ears extend under the opening to keep the fastener in place in the housing.

23. A catheter comprising:

a catheter body having a tubular wall, proximal and distal ends, and at least one lumen extending therethrough;

a control handle mounted to the proximal end of the catheter body, the control handle comprising:

a housing having proximal and distal ends, a tubular core within the housing and fixedly attached to the housing and catheter body;

an interior member within the housing having proximal and distal ends and being longitudinally moveable relative to the housing and tubular core;

a washer comprising a proximal ring and an outer wall extending distally therefrom mounted about the tubular core;

a flexible o-ring having inner and outer surfaces and sitting within the washer so that the outer surface of the o-ring is in contact with the outer wall of the washer and the inner surface of the o-ring is in contact with the core;

a thumb control knob threadably-engaged to the distal end of the interior member; whereby, when the thumb control knob is screwed onto the proximal piston, it compresses the o-ring into the washer, pressing the inner surface of the o-ring against the core so that the user can adjust the tension on the thumb control by screwing or unscrewing the thumb control.

\* \* \* \* \*